United States Patent
Olofsson

[11] Patent Number: 6,156,059
[45] Date of Patent: Dec. 5, 2000

[54] SCALP COOLING APPARATUS

[76] Inventor: Yvonne Olofsson, Trädgårdgatan 15 A, 223 53, Lund, Sweden

[21] Appl. No.: 09/284,706
[22] PCT Filed: Oct. 16, 1997
[86] PCT No.: PCT/SE97/01735
§ 371 Date: Apr. 16, 1999
§ 102(e) Date: Apr. 16, 1999
[87] PCT Pub. No.: WO98/16176
PCT Pub. Date: Apr. 23, 1998

[30] Foreign Application Priority Data

Oct. 17, 1996 [SE] Sweden .................................. 9603824

[51] Int. Cl.⁷ ....................................................... A61F 7/00
[52] U.S. Cl. ............................................. 607/109; 607/110
[58] Field of Search ............................... 607/96, 104, 108, 607/109, 110, 111

[56] References Cited

U.S. PATENT DOCUMENTS 2,049,723  8/1936  Pomeranz .
4,172,495 10/1979  Zebuhr et al. ............................. 165/46
4,572,188  2/1986  Augustine et al. ..................... 128/380
5,658,324  8/1997  Bailey, Sr. et al. ..................... 607/104

FOREIGN PATENT DOCUMENTS 0158470 10/1985  European Pat. Off. .
9000752  3/1990  Netherlands .
89/04184 12/1982  WIPO .
89/09583 10/1989  WIPO .

Primary Examiner—Linda C. M. Dvorak
Assistant Examiner—R. Kearney
Attorney, Agent, or Firm—Hayes, Soloway, Hennessey, Grossman & Hage, PC

[57] ABSTRACT

The present invention relates to an apparatus for regulating the temperature of the scalp of a person undergoing chemotherapy or like treatment, for instance. The apparatus comprising a head covering (1) that includes a plurality of chambers (4) that extend from the edge (5) of the head covering up towards the crown (7) of said covering, such that the coolant inlets (9) are located at the bottom of the head covering in the vicinity of its edge (5) and the outlets (10) are located at the top of the head covering in the vicinity of its crown (7).

5 Claims, 2 Drawing Sheets

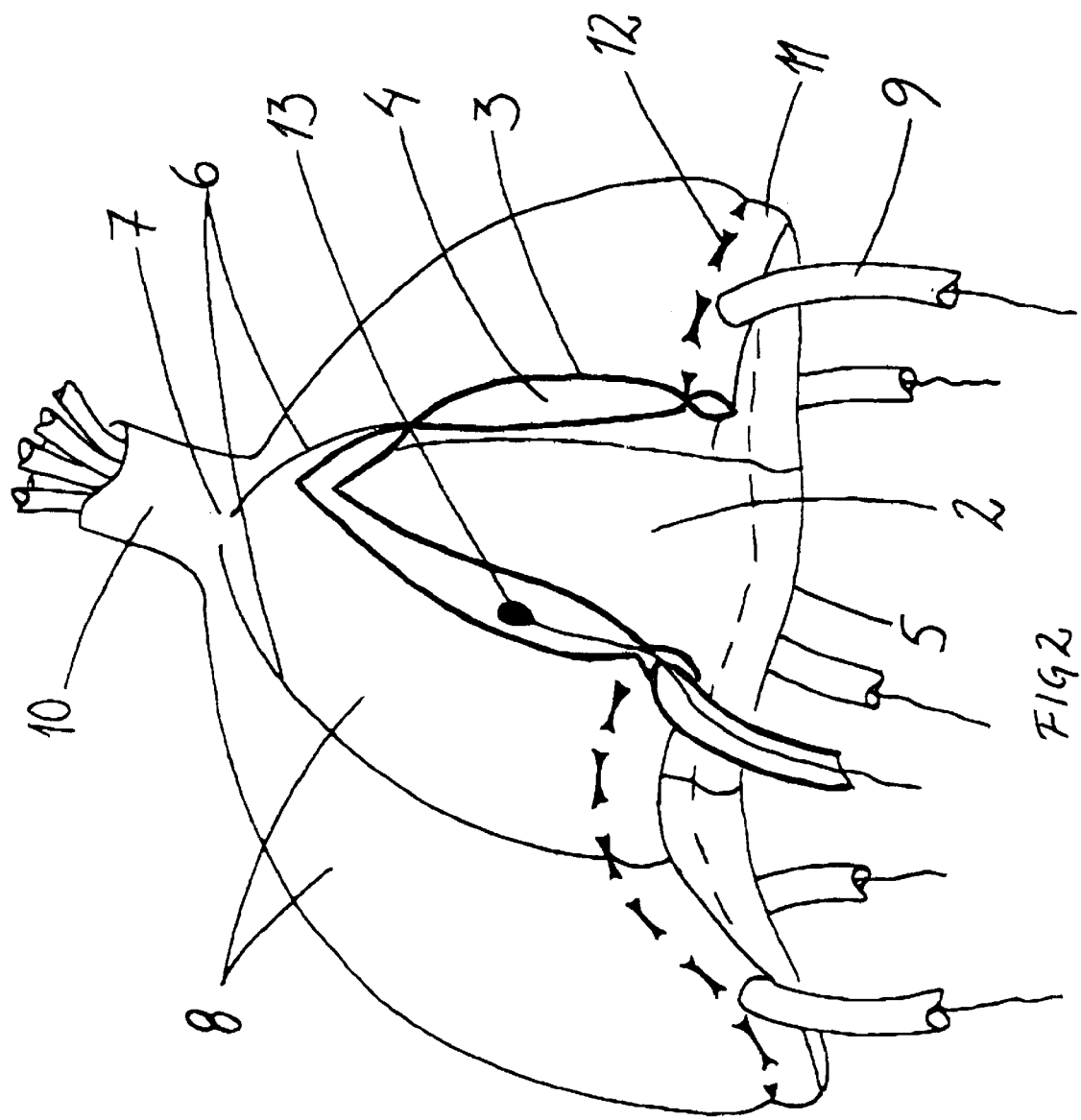

SCALP COOLING APPARATUS

The present invention relates to a method and to apparatus for regulating the temperature of the scalp of a human being undergoing chemotherapy or like treatment, for instance.

It is known that the problem of lows of hair suffered by patients undergoing chemotherapy can be alleviated, and in some cases fully eliminated, by cooling the hairy part. It has been observed that cooling of the skin, and therewith the roots of the hair, to a temperature of from ±0° to ±5° C. reduces the ability of the roots to take-up the treatment preparation and therewith increases the chances of the roots surviving the treatment to a corresponding extent, wherewith the patient keeps his/her hair. According to known techniques, this cooling treatment will preferably be continued for one to five hours.

In the case of one known apparatus, a head covering, in the form of a bonnet, consisting of a soft-frozen gel block is placed on the patient. The block is heavy and often has a temperature of below −18° C., when the bonnet is placed on the head of the patient, which is normally wet in these circumstances. Because the bonnet is inflexible and initially very cold, the device is uncomfortable. Another problem is that the frozen blocks quickly melt and does not therefore keep the temperature beneath the upper temperature limit during the whole of the treatment period. It is necessary for the patient to change bonnets, often as soon as about forty-five minutes after having donned the head covering, when the temperature has risen from −18° C. to above +10° C.

In the case of another known apparatus, the patient is fitted with a head covering that is continuously cooled. This head covering is comprised of two layers which define therebetween a space through which a cooling fluid flows. The space in the head covering is connected by means of at least one hose to a cooling unit that supplies the head covering with fluid, wherewith cooling of the scalp can take place with continuously applied cold and at a relatively constant temperature during the whole of the treatment period. This obviates the need for the patient to place a stiff, super-cooled covering on his/her head. The fluid inlet and outlet are preferably distributed over the head covering, so as to obtain good circulation and therewith uniform cooling of the entire scalp.

This head covering is also heavy to carry during the treatment period, and it is proposed to supplement said covering with a suspension means that will relieve the load on the patient's neck. Another problem resides in keeping down the temperature around the edges of the head covering.

Different parts of the head and the scalp have different concentrations of blood vessels and therefore different cooling requirements, which cannot be satisfied with known cooling devices. As a result, the patient is either cooled to an unnecessary extent in some regions or, as in the case when the cooling effect is determined by the temperature at a region in which the blood vessels are less dense, insufficiently at other regions. It has also been observed that the cooling effect required is greater at the bottom around the hairline of the patient and around his/her temples than at the top.

The object of the present invention is to overcome the aforesaid problems and to provide an improved method and an improved apparatus of the aforesaid kind.

This object is achieved with a method and an apparatus according to the accompanying independent claims.

These and other objects of the present invention will be apparent to the skilled person who has studied the following detailed description of a preferred embodiment of the invention. The description is made with reference to the accompanying drawings, in which identical or similar parts have been identified with the same reference signs.

FIG. 2 is a partially broken view of the apparatus shown in

Figure 1:
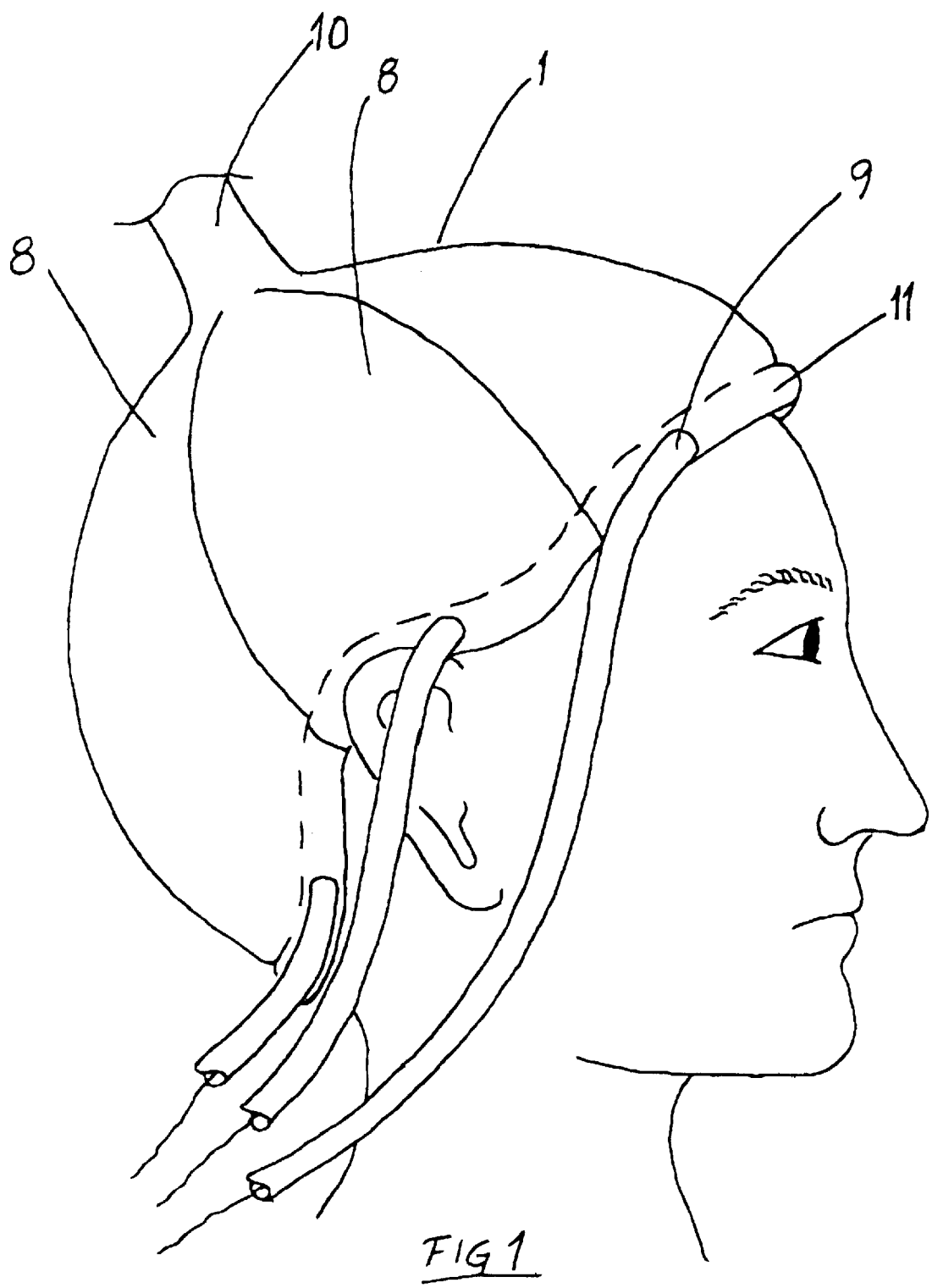
FIG. 1 illustrates an apparatus according to one embodiment of the present invention.

FIG. 1 shows a head covering 1 according to a preferred embodiment of the invention, with the head covering applied to a patient's head for the purpose of cooling the patient's scalp. The inventive head covering, or bonnet, is made of an elastic material so that it will seat against the head of the patient and remain in place without being dislodged from the patient should he/she change the position of his/her body during treatment. The bonnet may also be supplemented with a chin strap for instance, it so desired.

The material from which the bonnet is made will also be capable of enclosing a cooling fluid intended for circulation between walls embodied in th bonnet, in the manner described in more detail hereinafter, without the fluid leaking from the bonnet.

In the case of the illustrated embodiment, the bonnet is produced from a rubber fabric. It will be understood, however, that this fabric is only an examples of possible materials that can be used and does not constitute a limitation to the scope of the invention. Different types of elastic, impervious plastic materials or coated and therefore densely net-formed material structures can also be used to advantage.

The bonnet includes an inner fabric 2 which lies proximal to the patient's head, and externally of the fabric 2 an outer fabric 3. The fabrics define there between a space 4 through which cooling fluid shall flow. The fabrics are joined together at their bottom regions around the edge 5 of the bonnet and also along lines 6 that extend up from said edge towards the crown 7 of the bonnet, centrally at the top of the bonnet. These lines thus form wedge-shaped sections 8 that include separate section chambers 4. These sections may be from four and upwards in number, preferably from six to eight. The number of sections determines the size of those scalp zones that can be regulated individually.

Provided at the bottom of each section is an inlet 9, while the upper part of the bonnet includes an outlet 10 for flow connection of the bonnet to a cooling unit, not shown. The inlet will preferably be placed as close as possible to the edge 5 and is constructed to distribute the inflowing coolant uniformly along the bottom edge of the entire section chamber.

In one preferred embodiment, a channel 11 is formed along the bottom edge of the section and the inlet 9 is located in the channel. The channel includes a plurality of openings through which coolant flows into the section chamber. The channels and the openings may be obtained by a broken join 12 formed at a distance from and generally parallel with the edge 5.

The inlet may also be provided with a coolant spraying device, or spreader, along the bottom, internal edge of the section. This spray device may, for instance, include a hose that has a row of coolant-spraying holes or openings along its length.

An individual supply conduit extends from a cooling unit to each section. It is desired to regulate the temperature and/or the flow in each section, so as to adjust the cooling effect on the basis of local cooling requirements.

Arranged in the interior of each section chamber 4 is a temperature sensor 13 which monitors the current local temperature. In one embodiment, the sensor may be electric and the temperature reading delivered via a cable. This cable may be drawn out of the section through the inlet or the outlet and passed out through the conductor wall at an appropriate position. The sensor will preferably lie in abutment with the inner fabric wall 2.

The temperature sensor may alternatively be mounted in the interior of the bonnet, which simplifies the delivery of information from the temperature sensor and slightly enhances monitoring precision. In one embodiment, the sensor may be mounted on or in the inner fabric wall 2, for instance in immediate contact with the head, inwardly of respective sections.

Monitoring of the local temperatures in each section enables the temperature and/or the rate of flow of the coolant delivered to respective sections to be regulated or controlled so that all sections will obtain precisely that cooling effect which is required to block the absorbency of the scalp, neither more nor less.

This regulation can be effected manually after manually reading the temperatures, or automatically with the aid of an electronic monitoring and regulating means.

With the aid of simple apparatus, a desired set point value, e.g. +5° C. can be compared in a computer with current information from the temperature sensors in respective sections, said computer functioning to initiate adjustment of the cooling effect in each section in relation to the difference.

With the object of lessening the discomfort of the patient still further, such an apparatus may include a program for regulated cooling. The bonnet may be at room temperature when placed on the patient's head and the patient given the choice of lowering the temperature rapidly or slowly.

With the intention of preventing power losses, and therewith a reduction in the requisite fluid volume in each section, the bonnet may be provided externally with an outer insulating guard. This guard may, for instance, include a heat-radiation reflecting and/or a porous insulating material. Particularly preferred in this respect is an outer bonnet or head covering that comprises several layers which include separate air-filled cavities or channels that function to counteract conduction, radiation and convection of heat.

The outlets 10 from respective sections are arranged at the top of the bonnet, i.e. also centrally of the top of the patient's head, where the cooling-effect requirement is lowest. Bach of the outlets is preferably connected to a respective conduit for returning fluid to the cooling unit. These conduits may, however, be contained inside a coarser conduit, or gathered together by some suitable mans in order to keep down the number of loosely lying conduits around the patient. In one alternative embodiment, the outlets nay alternatively be combined in a return conduit.

In one preferred embodiment, a cooling unit may be used for each section, so that flow rate and temperature can be regulated individually for each section. In one alternative embodiment, there is used a single cooling unit with which there is used a common temperature for the cooling fluid supplied to the sections. The cooling effect can then be regulated, by throttling the flow of fluid.

The joints can be produced by any means suitable in respect of the material chosen. In the case of rubber, the joints may be vulcanized or glued. In the case of thermoplastics, the joints may be glued or wolded, e.g. high-frequency welds, etc.

The materials will preferably be elastic so as to sit around the patient's head. Moldability assists in ensuring that the inner wall or the inner fabric of the sections will lie against the whole of the scalp so that no part of the scalp will go untreated.

The cooling fluid used may be any fluid known to the skilled person in this particular technical field and suitable for the temperature intervals and cooling units concerned.

What is claimed is:

1. Apparatus for regulating the temperature of a human scalp, comprising a head covering (1) that includes a flow passage and a cooling fluid which flows through the passage from an inlet (9) at the edge of the head covering to an outlet (10) at the crown of said head covering and which is connected to a circulating system, characterized in that the head covering includes a plurality of mutually delimited, converging chambers (4) which extend from the edge (5) of the head covering up to the crown (7) of said covering; in that a temperature sensor (13) is mounted in connection with each flow passage (4) for registering local temperature; and in that a regulating device is provided for individually regulating the temperature or the flow of the fluid flowing through respective flow passages.

2. Apparatus according to claim 1, characterised in that a channel (11) in arranged along the bottom edge (5) of the head covering in each flow passage (4); in that the inlet (9) is connected to the channel (11); and in that a plurality of openings are disposed between the channel and the flow passage for providing uniform distribution of the fluid across the width of the flow passage.

3. Apparatus according to claim 1, characterized in that the head covering includes an insulating outer cover.

4. Apparatus according to claim 1, characterized in that the head covering comprises an inner fabric (2) for abutment with a patient's head, and an outer fabric (3) arranged externally of said inner fabric; in that the fabrics are joined together along the bottom edge (5) of the head covering and along lines (6) that extend from said edge up towards the crown (7) of the head covering, therewith to define wedge-shaped sections (8) that enclose individual section chambers.

5. Apparatus according to claim 4, characterized in that the number of sections is greater than four.

* * * * *